(12) United States Patent
Kirchholtes et al.

(10) Patent No.: US 6,969,708 B1
(45) Date of Patent: Nov. 29, 2005

(54) PROCESS FOR THE PREPARATION OF A HIGH PURITY COMPOSITION COMPRISING (7α, 17α)- 17-HYDROXY-7-METHYL-19-NOR-17-PREGN-5(10)-EN-20-YN-3-ONE

(75) Inventors: Peter H. G. M. Kirchholtes, Oss (NL); Gerard A. J. M. T. Sas, Veghel (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/787,215

(22) PCT Filed: Oct. 11, 1999

(86) PCT No.: PCT/EP99/07768

§ 371 (c)(1),
(2), (4) Date: May 17, 2001

(87) PCT Pub. No.: WO00/23460

PCT Pub. Date: Apr. 27, 2000

(30) Foreign Application Priority Data

Oct. 16, 1998 (EP) .................................. 98203460

(51) Int. Cl.⁷ .......................... A61K 31/56; C07J 53/00
(52) U.S. Cl. ...................... 514/177; 514/178; 552/500; 552/501
(58) Field of Search ................ 514/177, 178; 552/501, 500

(56) References Cited

U.S. PATENT DOCUMENTS

| | | |
|---|---|---|
| 3,340,279 A | 9/1967 | De Jongh et al. |
| 3,432,528 A | 3/1969 | Anner et al. |
| 3,475,465 A | 10/1969 | De Winter et al. |
| 3,576,828 A | 4/1971 | Anner et al. |
| 6,187,339 B1 | 2/2001 | de Haan et al. |

FOREIGN PATENT DOCUMENTS

| | | |
|---|---|---|
| EP | 0 159 739 A | 10/1985 |
| EP | 0 389 035 A | 9/1990 |
| EP | 0 613 687 A | 7/1994 |
| EP | 0 707 848 A | 4/1996 |
| EP | 0 707 848 A1 | 4/1996 |
| FR | 1 583 441 A | 10/1969 |
| WO | WO 89 09058 A | 10/1989 |
| WO | WO 98 39012 A | 9/1998 |
| WO | WO 98/39012 A1 | 9/1998 |
| WO | WO 98 47517 A | 10/1998 |
| WO | WO 98/47517 A1 | 10/1998 |

OTHER PUBLICATIONS

Van Vliet N P et al: "An Alternative Synthesis of 17.beta.-hydroxy-7.alpha.-methyl-19-nor-17.alpha.-pregn-5(10)-en-20-yn-3-one (Org OD 14)" Recueil des Travaux Chimiques des Pays-Bas., vol. 105, No. 4, Apr. 1986, pp. 111-115.

Declercq J P et al: "Conformational analysis of 3-oxo 5(10)-unsaturated steroids. Single-crystal x-ray structure analysis of 17-hydroxy-7.alpha.-methyl-19-nor-17.alpha.-pregn-5(10)-en-20-yn-3-one (Org OD 14)" Recueil des Travaux Chimiques des Pays-Bas., vol. 103, No. 5, May 1984, pp. 145-147.

Wieland P et al: "Steriods. CCXI. Synthesis of 7.alpha.-methyl-3-oxo-19-norandrosta-4,9, 11-trienes" Helvetica Chimica Acta, vol. 50, No. 6, Sep. 21, 1967, pp. 1453-1461.

European Search Report, European Application No. EP 02 02 2689, dated Jan. 31, 2003 (3 pages).

Roberts, Royston M., et al., "Modern Experimental Organic Chemistry," 50-51, 63, 66-72 (4th ed. CBS College Publishing 1985).

Communication of a Notice of Opposition, Jan. 30, 2004, Opponent—Norton Healthcare Limited.

Communication of a Notice of Opposition, Feb. 9, 2004, Opponent—Helm AG.

Communication of a Notice of Opposition, Feb. 9, 2004, Opponent—Industriale Chimica S.r.l.

Communication of a Notice of Opposition, Feb. 9, 2004, Opponent—Zentiva a.s.

Communication of a Notice of Opposition, Feb. 9, 2004, Opponent-Tecnimede, Sociedade Tecnico—Medicinal S.A.

Petition, Feb. 8, 2004, Petitioner—Arrow Generics Limited.

English Translation of Communication of a Notice of Opposition, Feb. 9, 2004, Opponent-Helm AG.

English Translation of European Patent No. 1 121 375 dated Apr. 19, 2004.

Closed Record in the Petition of Arrow Generics Limited for Revocation of Claims in European Patent EP 1 121 375 B1. (May 11, 2004).

Communication of proprietor Akzo Nobel with European Patent Office regarding Oppositions to EP 1 121 375 B1 (Oct. 15, 2004).

(Continued)

Primary Examiner—Shaojia Anna Jiang
(74) Attorney, Agent, or Firm—TraskBritt

(57) ABSTRACT

The invention pertains to a process for the preparation of a high purity composition of (7α, 17α)-17-hydroxy-7-methyl-19-nor-17-pregn-5(10)-en-20-yn-3-one. The process provides for a composition with less than 0.5% of (7α, 17α)-17-hydroxy-7-methyl-19-nor-17-pregn-4-en-20-yn-3-one. This composition can be used as a source for the preparation of stable pharmaceutical dosage units.

12 Claims, No Drawings

OTHER PUBLICATIONS

Letter from Cavelier regarding Opposition against Columbian Patent Application 99065751 filed Oct. 15, 1999 (Jun. 2, 2004).

Schouten et al., Structure of the Triclinic Modification of 17beta-Hydroxy-19-nor-7 alpha-methyl-17alpha-pregn-5(10)-en-20-yn-3-one (ORG OD14), 1991, pp. 1754-1756, International Union of Crystallography (1991).

Expert Report of Dr. Roger Newton in the Petition of Arrow Generics Limited for Revocation of Claims in European Patent EP 1 121 375 B1 (Oct. 16, 2004).

V. Alexéev, Análise Quantitativa, pp. 97-98 (Livraria Lopes da Silva, eds. Portugal).

Levine et al. Hungarian Patent Application 160797 (Oct. 30, 1973).

Waters, An Introduction to Practical Organic Chemistry, pp. 1-35 (London, UK 1934).

Defences and Counterclaim, In the Court of Session, Intellectual Property Cause, Organon Labs, Ltd et al. v. Norton Healthcare (United Kingdom, 2004).

Presentation of Laboratorios Recalcine S.A. against Chilean Patent Application 2343-1999 (Jul. 29, 2003). (English language translation).

Opposition by Gynopharm S.A. against Columbian Patent Application file number 99065751 (Columbia, Dec. 2, 2002). (English language translation).

Opposition against application for Ecuadorian patent No. SP-99-3181 (Ecuador 2000).

PROCESS FOR THE PREPARATION OF A HIGH PURITY COMPOSITION COMPRISING (7α, 17α)- 17-HYDROXY-7-METHYL-19-NOR-17-PREGN-5(10)-EN-20-YN-3-ONE

This application is a 371 of PCT/EP99/07768, filed Oct. 11, 1999, which claims priority to EUROPEAN PATENT OFFICE (EPO) 98203460.5, filed Oct. 16, 1998.

The invention relates to a high purity composition comprising (7α, 17α)-17-hydroxy-7-methyl-19-nor-17-pregn-5(10)-en-20-yn-3-one, a method for the preparation of this compound for use in the pharmaceutical composition as well as a pharmaceutical composition prepared by admixing a pharmaceutically suitable carrier and the high purity composition.

The compound (7α, 17α)-17-hydroxy-7-methyl-19-nor-17-pregn-5(10)-en-20-yn-3-one (Tibolone) having the structural formula 1:

Formula 1

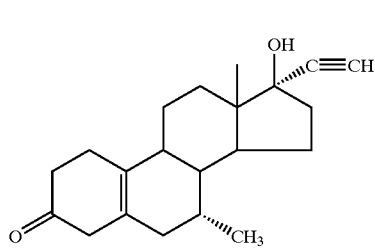

is known, for example from U.S. Pat. No. 3,340,279 and U.S. Pat. No. 4,701,450. The method described in these patents leads to a compound having combined oestrogenic, progestagenic and androgenic characteristics. This compound is used in medicaments having gonadomimetic, ovulation-inhibiting or immuno-modulating action.

Compositions comprising Tibolone and a pharmaceutically acceptable solid carrier have been described in EP 389 035, which disclosure is incorporated herein by reference. Tablets are available on the market under the name of Livial®.

The known tablets can be stable stored very well for, typically, 2 years at ambient temperature. A sufficiently humid atmosphere (e.g. 50–70% relative humidity) makes for a better storage stability than a relatively dry atmosphere (e.g. 45% relative humidity or below that).

A problem in the preparation of pharmaceutical dosage units is that during the preparation the relative amount of impurities may increase. In particular, the amount of one of the impurities which is already present in the bulk preparation i.e. (7α, 17α)-17-hydroxy-7-methyl-19-nor-17-pregn-4-en-20-yn-3-one (Org OM38) tends to increase during the process of making pharmaceutical dosage units. It is furthermore known that the amounts of Org OM38 in compositions comprising Tibolone increase upon storage.

The end of shelf life specification with respect to the amount of Org OM38 formed during storage is 5%. A minimum acceptable shelf life period for these dosage units is 1 year. It is an object of the present invention to improve upon the storage stability i.e. to enhance the shelf-live of the dosage units.

The customary amount of Tibolone in the known dosage unit is 2.5 mg in tablets or capsules of 100 mg, i.e. 2.5%. For the sake of providing therapies better tailored to the individual woman's needs, it is desired to provide dosage units having a lower amount.

However, adaptation of a known formulation by simply including a lower amount of Tibolone further decreases the stability of the dosage unit substantially. E.g., if a 2.5 mg Tibolone dosage unit has a shelf-life of, e.g., 2–3 years at room temperature, the same unit upon lowering the amount of Tibolone to e.g. 0.3 mg can only be kept at 4° C. for a period of 6–12 months. Such a lower stability is unacceptable in daily practice. It is a further object of the invention to provide dosage forms having a lower content of Tibolone (which are more prone to stability problems than regular dosage forms) and that can be suitably kept for a prolonged period of time.

One of the possibilities to keep the amount of Org OM-38 below a desired level also after a prolonged storage time is to limit the amount initially present in the bulk preparation. Thus, there is a need to synthesize high purity Tibolone batches with a low contamination content of Org OM-38. It is an object of the present invention to provide for such high purity batches of Tibolone.

During the last step of the synthesis of Tibolone a solution of (7α, 17α)-3,3-dimethoxy-17-hydroxy-7-methyl-19-norpregn-5(10)-en-20-yn-3-one in a mixture of pyridine and ethanol is mixed with a solution of oxalic acid in water and the mixture is stirred for 3 hours at approximately 30° C. The solution is then poured out in a mixture of pyridine and water and the resulting suspension is filtered. The crystals are washed with a mixture of water and pyridine and subsequently, the crystals are dried under vacuum at 40° C. to give (7α, 17α)-17-hydroxy-7-methyl-19-norpregn-5(10)-en-20-yn-3-one (see also van Vliet et al (1986), Recl. Trav. Chim. Pays-Bas 105, 111–115).

As this compound has a lower stability than the corresponding (7α, 17α)-17-hydroxy-7-methyl-19-nor-pregn-4-en-20-yn-3-one there is always formed a small percentage of the latter compound via acid catalyzed isomerisation. Furthermore, this isomerisation takes place at higher temperature and upon long term storage of the crystals Unexpectedly, it now has been found that the rate of formation of Org OM38 during drying and storage in a specific batch can be decreased if crystals of Tibolone are washed with water and are allowed to age for at least 24 hours in the presence of water. Thus, the Tibolone is left for at least 24 hours under wet conditions. Preferentially the crystals are left under these conditions for a period of at least 3 days. There is no limit to a maximum period but a period of 3–6 days is best suited. The aging temperature preferentially is room temperature.

Thus according to the procedure of the present invention highly pure Tibolone with a low Org OM38 impurity is obtained by including a delay of several days before drying. The procedure reliably results in batches of Tibolone having a low Org OM38 content. A further advantage is that these batches have an excellent stability. Furthermore, these batches do not form additional amounts of the latter compound upon heating or long term storage.

The crystal formation procedure of the present invention can perfectly well be combined with the last step of the Tibolone synthesis wherein (7α, 17α)-3,3-dimethoxy-17-hydroxy-7-methyl-19-norpregn-5(10)-en-20-yn-3-one in a mixture of pyridine and ethanol is mixed with a solution of oxalic acid in water. In general, this reaction proceeds under mild acidic conditions in the presence of an organic solvent and water within a pH range of 5–3, preferentially 3.5–4.5. The acid preferentially is a weak organic acid having a pKa value in the range 1–5 such as citric acid, malonic acid, oxalic acid, dichloroacetic acid and acetic acid, optionally buffered with a base such as pyridine. As organic solvent e.g. ethanol, methanol, acetone, 2-propanol or tetrahydrofuran can be used. The solution is then poured out in water, which is made slightly alkaline by addition e.g. of a low amount of pyridine. After filtering the suspension the crystals are washed with a mixture of water made slightly alkaline by e.g. pyridine. Before drying the crystals are left wet for at least 24 hours.

Inclusion of the crystal aging step according to the invention results in bulk Tibolone batches with a low Org OM38 content. Routinely, batches are obtained with an Org OM38 content of less than 0.5%. Often even batches with less than 0.25% or even 0.1% of Org OM38 are obtained. Thus high purity compositions with Tibolone having less than 0.5% of Org OM38, preferably 0.25%, more preferably 0.10% of Org OM38 form part of the present invention. The amount of Org OM38 is calculated as the percentage (w/w) of the total amount of the bulk substance including some minor impurities. The amount of Tibolone usually is more than 98%.

The batches of these high purity Tibolone compositions with their low initial Org OM38 content are perfectly well suited to be used as a source for the preparations of pharmaceutical formulations. This guarantees a formulation with a low initial Org OM38 content and improves therefore its storage properties. Pharmaceutical preparations prepared with high purity Tibolone usually result in preparations with less than 1% of Org OM38, often even less than 0.7% of Org OM38 and these preparations are less prone to increase in Org OM38 content during storage.

As indicated before the amount of Org OM38 in a dosage form also depends upon the concentration of the active substance, the amount of impurity being higher as the amount of Tibolone in the dosage unit decreases. Therefore, using high purity Tibolone as the active substance, dosage units can now been prepared with a lower amount of Tibolone and still having an acceptable shelf life. Thus, the invention also relates to pharmaceutical dosage units, which can be prepared by admixture of a pharmaceutically suitable solid carrier and the high purity composition of the present invention.

A typical known formulation for Tibolone is a 100 mg dosage unit having 2.5 mg of Tibolone contained therein, a relatively small amount (e.g. approximately 1% by weight) of pharmaceutically acceptable auxiliaries, and a carrier making up the body of the tablet. The carrier typically is composed of 10% by weight of starch, e.g. potato starch, and 90% by weight of lactose.

Due to the excellent stability properties of dosage units with a lower amount of active substance than the present commercially available tablets of 2.5 mg active substance, the present invention now makes it also possible to provide for stable dosage units comprising Tibolone in an amount of less than 2.50 mg, preferably 1.25 mg or less, more preferably 0.625 mg or less. At a shelf life of 1.5 years, preferably 2 years these dosage units still comprise less than 5% of OM38 (relative to the amount of Tibolone).

It is another aspect of the present invention to provide dosage units comprising Tibolone in amounts of less than 2.50 mg, preferably 1.25 mg or less, more preferably 0.625 mg or less and comprising at a shelf life of 6 months less than 3%, preferably 2% of OM38. The shelf life preferably is extended up to 1 year, preferably 1.5 year, more preferably 2 years.

As used herein shelf life means storage during a specified period under temperature conditions varying from 2–25° C. Dosage units can be packed e.g. in push-through packs (PTP, blister) and are preferably stored in dark (e.g. enclosed in carton). Alternatively they might also be stored in bottles e.g. high-density polyethylene bottles.

The pharmaceutical dosage units of the present invention will generally take the form of tablets or capsules, but other solid or dry pharmaceutical preparations are included.

Methods for making such dosage units are well known. For example in the standard English language text Gernaro et al., Remington's Pharmaceutical Sciences, (18$^{th}$ ed., Mack Publishing Company, 1990, see especially. Part 8: Pharmaceutical Preparations and Their Manufacture), methods of making tablets, capsules and pills and their respective components are described.

Tablets and capsules are prepared of granulates using dry or wet granulation techniques as disclosed in The Theory and Practice of Industrial Pharmacy (Third edition) L. Lachman, H. A. Lieberman and J. L. Kanig (1986) p 1–99 and 293–345.

The aim of granulation is to improve the flowability and compressibility of the powder mixture. Wet granulation forms the granules by binding the powders (a mixture of a diluent and disintegrant) together with an adhesive. The wet granulation technique employs a solution, suspension or slurry containing a binder, which is usually added to the powder mixture; however the binder may be incorporated dry to the powder mix and the liquid may be added by itself. The wet granulation process is performed in mixers/kneaders or fluid bed systems.

Usually an amount of water is incorporated in the basic granulate ranging from 5.5–7%. Preferably the amount of water incorporated is at least 6%.

After granulation the mass is dried to the desired water content using fluid bed dryers, tray dryers, vacuum dryers or other suitable dryers.

To attain a good distribution of the active (Tibolone) over the total mass, the active is premixed with a part of the granulate, sieved using an oscillating sieve, a high speed sieve or other suitable sieving equipment. Next this mixture is mixed with the remaining part of the granulate and a lubricant. This mixture is compressed to tablets, or filled into capsules.

The following examples are illustrative for the invention and should in no way be interpreted as limiting the scope of the invention.

EXAMPLES

Example 1

A solution of (7α, 17α)-3,3-dimethoxy-17-hydroxy-7-methyl-19-norpregn-5(10)-en 20-yn-3-one (15 kg) in a mixture of pyridine (630 ml) and ethanol (315 liters) was mixed with a solution of oxalic acid (750 gr) in water (90 liters) and the mixture was stirred for 2 hours at approximately 30° C. The solution was poured out in a mixture of pyridine (1350 ml) and water (300 liters) and the resulting suspension was filtered. The crystals were washed with a mixture of water and pyridine and dried under vacuum at 40° C. to give (7α, 17α)-17-hydroxy-7-methyl-19-norpregn-5(10)-en-20-yn-3-one containing 0.6% of the corresponding (7α, 17α)-17-hydroxy-7-methyl-19-norpregn-4-en-20-yn-3-one as indicated by HPLC analysis; a stress test at 45° C. (duration 1 month) indicated a 0.4% increase of the latter compound.

Example 2

A solution of (7α, 17α)-3,3-dimethoxy-17-hydroxy-7-methyl-19-norpregn-5(10)-en-20-yn-3-one (15 kg) in a mixture of pyridine (630 ml) and ethanol (315 liters) was mixed with a solution of oxalic acid (375 gr) in water (90 liters) and the mixture was stirred for 3 hours at approximately 30° C. The solution was poured out in a mixture of pyridine (1350 ml) and water (300 liters) and the resulting suspension is filtered. The crystals are washed with a mixture of water and pyridine and allowed to age for 3–6 days at room temperature. Subsequently, the crystals were dried under vacuum at 40° C. to give (7α, 17α)-17-hydroxy-7-methyl-19-norpregn-5(10)-en-20-yn-3-one containing ≦0.1% of the corresponding (7α, 17α)-17-hydroxy-7-methyl-19-norpregn-4-en-20-yn-3-one as indicated by HPLC analysis; a stress test at 45° C. (duration 1 week) indicated a <0.1% increase of the latter compound.

Example 3

The preparation as described in example 2 was repeated. (7α, 17α)-17-hydroxy-7-methyl-19-norpregn-5(10)-en-20-yn-3-one was obtained which contained 0.2% of the corresponding. (7α, 17α)-17-hydroxy-7-methyl-19-norpregn-4-en-20-yn-3-one as indicated by HPLC analysis; a stress test at 45° C. (duration 1 week) indicated a 0.1% increase of the latter compound.

Example 4

A basic granulate was prepared by granulation of a mixture of lactose (diluent), potato starch (disintegrant) and potato starch mucilage (binder) in a fluid bed granulator. The water content of the granulate varied within 5.5%–6.5%. After granulation, the basic granulate was passed through a conical high speed sieve. Part of the granulate (10% w/w) was mixed with Tibolone and ascorbyl palmitate using a tumble blender and then passed through a conical high speed sieve.

The Tibolone premix and the remainder of the basic granulate were mixed in a ribbon blender. Magnesium stearate was added and mixed. The final granulate was compressed into round tablets.

The stability of the active compound (Tibolone) in tablets was determined.

TABLE 1

Content of decomposition product (Org OM38) in percentage of the declared amount of Tibolone per tablet, in tablets containing a various amount of Tibolone, after storage at 25° C. and 60% relative humidity.

| | Concentration of Tibolone per tablet | | | |
|---|---|---|---|---|
| | 0.46 | 0.96 | 1.92 | 2.5 |
| Storage time (months) | Amount of Org OM38 formed during storage (in percentage of the declared amount of tibolone) | | | |
| 0 | 1.2 | 0.8 | 0.5 | 0.4 |
| 6 | 6.5 | 3.5 | 1.8 | 1.6 |
| 12 | 9.5 | 5.1 | 2.7 | 2.2 |
| 18 | 12.2 | 6.1 | 3.3 | 2.7 |

Example 5

Tablets of 1.25 mg of Tibolone have been prepared as described in example 4. The tablets were stored at 25° C. and 60% relative humidity and the decomposition product (Org OM38) was measured.

TABLE 2

Content of decomposition product (Org OM38) in percentage of the declared amount of Tibolone per tablet. Stability of three development tablet batches (1.25 mg of Tibolone per 65 mg) was assessed (storage at 25° C. and 60% relative humidity).

| | Batch no | | |
|---|---|---|---|
| | 049514001 | 049515001 | 049516001 |
| Storage time (months) | Amount of Org OM38 formed during storage (in percentage of the declared amount of Tibolone) | | |
| 0 | 0.7 | 1.0 | 1.3 |
| 6 | 2.3 | 2.6 | 2.9 |
| 12 | 3.5 | 3.7 | 3.8 |
| 18 | 4.3 | 4.2 | 4.3 |
| 24 | 5.1 | 4.9 | 4.9 |

It can be concluded that the shelf life of tablets containing 1.25 mg of Tibolone per tablet of 65 mg is borderline.

Example 6

Tibolone as prepared as in example 2 was used as the active compound to prepare tablets as described in example 4. The amount of Org OM38 formed in several batches during storage was determined.

TABLE 3

The stability of six tablet batches (1.25 mg of Tibolone per 65 mg) was assessed (storage at 25° C. and 60% relative humidity). The amount of water incorporated in the basic granulate was varied from 6.0% to 6.5%.

| | Batch no | | | | | |
|---|---|---|---|---|---|---|
| | TD96.1128 | TD96.1132 | TD96.1133 | 162454001 | 162455001 | 162456001 |
| Storage time (months) | Amount of Org OM38 formed during storage (in percentage of the declared amount of Tibolone) | | | | | |
| 0 | 0.7 | 0.5 | 0.5 | 0.9 | 0.8 | 0.9 |
| 6 | 1.3 | 1.1 | 1.1 | 1.8 | 1.7 | 1.8 |
| 12 | 1.8 | 1.5 | 1.6 | | | |
| 18 | 2.0 | 1.5 | 1.7 | | | |

TABLE 3-continued

The stability of six tablet batches (1.25 mg of Tibolone per 65 mg) was assessed (storage at 25° C. and 60% relative humidity). The amount of water incorporated in the basic granulate was varied from 6.0% to 6.5%.

| | Batch no | | | | | |
|---|---|---|---|---|---|---|
| Storage time (months) | TD96.1128 | TD96.1132 | TD96.1133 | 162454001 | 162455001 | 162456001 |
| | Amount of Org OM38 formed during storage (in percentage of the declared amount of Tibolone) | | | | | |
| Water content of the basic granulate | 6.5 | 6.5 | 6.5 | 6.3 | 6.1 | 6.1 |

What is claimed is:

1. A process for reducing the rate of formation of (7α, 17α)-17-hydroxy-7-methyl-19-nor-17-pregn-4-en-20-yn-3-one impurity in crystals of (7α, 17α)-17-hydroxy-7-methyl-19-nor-17-pregn-5(10)-en-20-yn-3-one, wherein the (7α, 17α)-17-hydroxy-7-methyl-19-nor-17-pregn-5(10)-en-20-yn-3-one contains less than 0.5% by weight of (7α, 17α)-17-hydroxy-7-methyl-19-nor-17-pregn-4-en-20-yn-3-one as the impurity relative to (7α, 17α)-17-hydroxy-7-methyl-19-nor-17-pregn-5(10)-en-20-yn-3-one after drying, said process comprising:

aging crystals of (7α, 17α)-17-hydroxy-7-methyl-19-nor-17-pregn-5(10)-en-20-yn-3-one in the presence of water for a period of time of at least 24 hours.

2. The process of claim 1 wherein the period of time lasts 3–6 days.

3. The process of claim 1, wherein the crystals are formed in the last step of a synthesis comprising the steps of:
a. reacting (7α, 17α)-3,3-dimethoxy-17-hydroxy-7-methyl-19-norpregn-5(10)-en-20-yn-3-one in an organic solvent with a weak acidic aqueous solution,
b. pouring out the solution in water which is slightly alkaline, and
c. washing the crystals with water which is slightly alkaline.

4. The process of claim 1, wherein the process comprises:
(i) washing crystals of (7α, 17α)-17-hydroxy-7-methyl-19-nor-17-pregn-5(10)-en-20-yn-3-one with water,
(ii) aging crystals of (7α, 17α)-17-hydroxy-7-methyl-19-nor-17-pregn-5(10)-en-20-yn-3-one in the presence of water for a period of time of at least 24 hours, and
(iii) drying the (7α, 17α)-17-hydroxy-7-methyl-19-nor-17-pregn-5(10)-en-20-yn-3-one.

5. The process of claim 1, wherein the water is alkaline.

6. The process of claim 5, wherein the water is mixed with pyridine.

7. The process of claim 4, wherein the crystals are obtained by filtration after crystallization.

8. The process of claim 4, wherein the drying is carried out after at least 3 days.

9. The process of claim 1, wherein the impurity is less than 0.25% by weight.

10. The process of claim 9, wherein the impurity is less than 0.1% by weight.

11. The process of claim 4, wherein the impurity is less than 0.25% by weight.

12. The process of claim 8, wherein the impurity is less than 0.1% by weight.

* * * * *